United States Patent [19]
Kotani

[11] Patent Number: 4,857,166
[45] Date of Patent: Aug. 15, 1989

[54] REFERENCE ELECTRODE

[75] Inventor: Haruo Kotani, Miyanohigashi, Japan

[73] Assignee: Horiba Ltd., Kyoto, Japan

[21] Appl. No.: 124,690

[22] Filed: Nov. 24, 1987

[30] Foreign Application Priority Data

Nov. 29, 1986 [JP] Japan ................................ 61-286269

[51] Int. Cl.$^4$ ........................................... G01N 27/30
[52] U.S. Cl. .................................................... 204/435
[58] Field of Search ........................ 204/435, 419, 418

[56] References Cited

U.S. PATENT DOCUMENTS

| | | | |
|---|---|---|---|
| 3,431,182 | 3/1969 | Frant ................................ | 204/419 X |
| 3,562,130 | 2/1971 | Hoole et al. ..................... | 204/435 X |
| 3,657,093 | 4/1972 | Farren ................................ | 204/419 |
| 3,787,309 | 1/1974 | Neti et al. .......................... | 204/418 |
| 3,915,831 | 10/1975 | Riseman et al. .................... | 204/419 |
| 4,468,271 | 8/1984 | Pierson ............................ | 204/419 X |

OTHER PUBLICATIONS

Stanley E. Manahan, Anal. Chem., vol. 42, No. 1, pp. 128–129, (1970).
Ya. N. Voitovich et al., Soviet Electrochemistry, vol. 10, No. 3, pp. 385–388, Mar. 1974.
F. Clayton et al., High Temperature Science, vol. 5, No. 5, pp. 358–364, Oct. 1973.
H. R. Bronstein et al., J. Electrochem. Soc., vol. 119, No. 2, pp. 125–128, (1972).

Primary Examiner—G. L. Kaplan
Attorney, Agent, or Firm—Price, Gess & Ubell

[57] ABSTRACT

The reference electrode includes a liquid junction portion where an internal solution is brought into contact with a sample solution by a thin film member formed of a substance having a low solubility in water and aqueous solutions and mounted on the liquid junction portion so that leakage of the internal solution to a side of the sample solution can be almost completely prevented. The thin film member forming the liquid junction portion is made of $MgF_2$ or $CaF_2$. A limiting equivalent ionic conductivity of a cation and that of a anion, which are comparatively large, and a transfer coefficient of the cation and that of the anion are nearly equal to each other so that a low solubility in water and aqueous solution can be realized to the extent that it is almost the same if the internal solution was brought into direct contact with the sample solution. In addition, an interliquid differential potential can be reduced and stabilized and high accuracy of measurement and reliability can thus be secured.

12 Claims, 5 Drawing Sheets

REFERENCE ELECTRODE

BACKGROUND OF THE INVENTION

1. Field of the Invention

The present invention relates to an improved electrode used as a standard electrode, also referred to as a reference electrode, standard electrode, assistant electrode and the like, for a measuring electrode (for example, a glass electrode) in the case where an ionic concentration (for example, pH) of a solution is measured.

2. Description of the Prior Art

A reference electrode is indispensable in the measurement of various kinds of ionic concentration and it is important that an inter-liquid potential difference that can show a small change be stabilized, regardless of the kind and concentration of a sample solution to be tested.

In a conventional reference electrode, as shown in FIG. 10, an internal electrode formed of, for example, a Ag electrode wire b, having a surface coated with AgCl, and an internal solution d formed of a 3.3 M-aqueous solution of KCl supersaturated with AgCl with a phosphoric acid buffer solution added are provided on a support pipe a formed of an electrically insulating glass. In order to construct a liquid junction, the internal solution d is brought into contact with the sample solution through a liquid junction member e formed of an inorganic sintered porous material, an organic high molecular porous material and the like, impregnated with, for example, KCl and positioned in a hole formed in a pointed end portion of the support pipe a. Referring to FIG. 10, reference mark f designates an internal solution make-up port provided with a cover g mounted on the support pipe a for permitting a make-up of any internal solution d that has been consumed.

That is to say, this conventional reference electrode provides a single pole cell schematically expressed by Ag/AgCl/3.3M-KCl/with a Liquid junction member (Sample solution). A potential $E_o$ generated in the Ag-/AgCl/3.3 M-KCl cell itself should be completely compensated, so that it will not appear in the measurement result, for example, by using the same one Ag/AgCl/3.3 M-KCl cell also in an internal electrode on a side of a measuring electrode (for example, a glass electrode). However, since the 3.3-M aqueous solution of KCl, which is the internal solution d, is diffused into the sample solution in the form of $K^+$ and $Cl^-$ through the liquid junction member e, an inter-liquid differential potential (referred to also as a differential diffusion potential) $E_D$, which cannot be compensated to some extent, cannot be avoided.

This inter-liquid differential potential $E_D$ can be expressed by the following equation:

$$E_D = (T^+ - T^-) \cdot \frac{R \cdot T}{F} \ln \frac{a_D}{a_{kc}}$$

wherein
- $T^+$: Transport coefficient of a cation n the internal solution d;
- $T^-$: Transport coefficient of an anion in the internal solution d;
- R: Ideal gas constant;
- T: Absolute temperature;
- F: Faraday constant;
- $a_D$: Activity of the sample solution; and
- $a_{kc}$: Activity of the internal solution.

Accordingly, in order to reduce and stabilize this inter-liquid differential potential $E_D$, it would be ideal if an internal solution d having a large limiting equivalent ionic conductivity and a transfer coefficient $T^+$ of a cation and a transfer coefficient $T^-$ of an anion equal to each other is used, and also that the concentration of the internal solution d be increased. This is one of the reasons why an aqueous solution of KCl of high concentration has been generally used as the internal solution d of the reference electrode.

Tables 1 and 2 showing a limiting equivalent ionic conductivity of main ions in an aqueous solution of 25° C., a transport coefficient of main electrolytes and a solubility of main electrolytes in an aqueous solution of 25° C., both the limiting equivalent ionic conductivity (73.5 cm $^{-1}$) of a cation $K^+$ constructed from KCl and the limiting equivalent ionic conductivity (76.35 cm $^{-1}$) of an anion $Cl^-$, also constructed from KCl, are comparatively large and nearly equal to each other. In addition, the transport coefficient $T^+$ (0.490) of a cation of KCl is nearly equal to the transport coefficient $T^-$ (0.509) of an anion of KCl.

Although crystalline KCl in theory could be satisfactorily used, KCl is an insulator and, therefore, a saturated aqueous solution of KCl having a high concentration has been frequently used. In addition, in the case where the sample solution contains a substance acting upon the aqueous solution of KCl, a disadvantage occurs in that gases are generated or compounds are deposited to destabilize the interliquid differential potential $E_D$ or clog the liquid junction member e, so that in such a case an aqueous solution of $KNO_3$ is used as the internal solution in place of the aqueous solution of KCl or an aqueous solution of $NH_4NO_3$ is used as an overcoat solution.

TABLE 1

| [Limiting equivalent ionic conductivity (cm $\Omega^{-1}$)] | | | |
|---|---|---|---|
| Cations | | Anions | |
| $H^+$ | 349.8 | $OH^-$ | 198.3 |
| $Rb^+$ | 77.8 | $Br^-$ | 78.14 |
| $K^+$ | 73.5 | $Cl^-$ | 76.35 |
| $Ag^+$ | 61.9 | $NO_3^-$ | 71.5 |
| $Ca^+$ | 59.5 | $CO_3^-$ | 69.3 |
| $Mg^+$ | 53.0 | $F^-$ | 55.4 |
| $Na^+$ | 50.1 | | |
| $Li^+$ | 38.6 | | |

TABLE 2

| [Transport coefficient of ions and solubility] | | | |
|---|---|---|---|
| Electrolyte | Transport coefficient $T^+$ of cation | Transport coefficient $T^-$ of anion | Solubility (mol/l) |
| KCl | 0.490 | 0.509 | 26.4 |
| $MgF_2$ | 0.489 | 0.510 | $8.4 \times 10^{-3}$ |
| $CaF_2$ | 0.517 | 0.482 | $1.6 \times 10^{-3}$ |

The above described conventional reference electrode has been used with an aqueous solution of KCl, as an internal solution d, which is diffused into a sample solution through a liquid junction member e formed of porous material. Since the aqueous solution of KCl is brought into contact with the sample solution and in order to prevent the contamination of the aqueous solution of KCl with the sample solution, the aqueous solution of KCl is positively leaked in the sample solution so that in the case where such a reference electrode is used, it is necessary to pay close attention to the following matters:

(A) The aqueous solution of KCl is maintained at an appointed constant concentration as far as possible;

(B) The aqueous solution of KCl is adapted to leak into a side of the sample solution (the sample solution is prevented from being mixed in the aqueous solution of KCl) by slightly heightening a pressure of the aqueous solution of KCl;

(C) Attention must be paid to the consumption of the aqueous solution of KCl and it is replenished if necessary;

(D) Attention must be paid to prevent any clogging of the liquid junction member e (a usual inter-liquid impedance amounts to several hundreds $\Omega$ to ten and several k$\Omega$) and the like.

Accordingly, a reference electrode having the above-described construction has exhibited many disadvantages in operation, maintenance and the like. In addition, even though sufficient attention could be paid to such matters, the generation of the inter-liquid differential potential $E_D$ cannot be avoided, so that it has been very difficult to achieve a highly accurate measurement.

SUMMARY OF THE INVENTION

The present invention was achieved in view of the problems of the above-described conventional conditions and it is an object of the present invention to provide a reference electrode capable of not only achieving a high accuracy of measurement and a high reliability, but also of remarkably improving its maintenance and operation. This is accomplished by adopting a novel construction of a liquid junction member capable of being reduced in size and capable of stabilizing the inter-liquid differential potential.

In order to achieve the above-described object, a reference electrode is provided for a liquid junction member and is characterized by a thin film member formed of $MgF_2$ or $CaF_2$, which is a substance having a transport coefficient of a cation and a transport coefficient of an anion nearly equal to each other and having reduced solubility in water and in aqueous solutions.

The reference electrode, according to the present invention, includes a liquid junction portion, where the internal solution is brought into contact with the sample solution by a thin film member formed of a substance having a remarkably reduced solubility in water and aqueous solutions (for example, about 1/1000 times that of KCl) mounted on the liquid junction portion so that any leakage of the internal solution to a side of the sample solution can be almost completely prevented. Accordingly, the internal solution and the liquid junction portion can be easily maintained under excellent conditions for a long period of time even though the conventionally required troublesome maintenance, such as described above, is not carried out. Moreover, since the thin film member forming the liquid junction portion is made of $MgF_2$ or $CaF_2$ (refer to Table 1 and Table 2), which is a substance having the fundamental properties of the internal solution, then a limiting equivalent ionic conductivity of a cation and that of an anion, which are comparatively large, a transfer coefficient of the cation and that of the anion nearly equal to each other and a remarkably reduced solubility in water and aqueous solution can be realized to the extent that it is almost the same if the internal solution was brought into direct contact with the sample solution. In addition, since the leakage of the internal solution into the sample solution can be completely prevented, and the dissolution of the thin film member constructing the liquid junction portion in the sample solution can be remarkably reduced, the inter-liquid differential potential can be reduced and stabilized and high accuracy of measurement and reliability can be secured.

BRIEF DESCRIPTION OF THE DRAWINGS

The preferred embodiments of the present invention are shown in FIGS. 1 to 9, in which.

DESCRIPTION OF THE PREFERRED EMBODIMENTS

The preferred embodiments of the present invention are below-described with reference to the drawings (FIGS 1 to 9).

Figure 1:
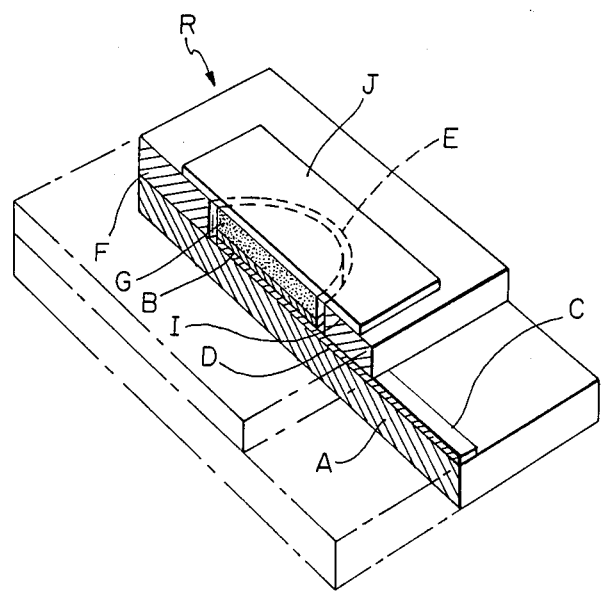
FIG. 1 is a partially sectioned perspective view showing an external appearance of a reference electrode according to a fundamental preferred embodiment.

FIG. 1 is a partially sectioned side view showing a reference electrode R according to a preferred embodiment. In this preferred embodiment, a sheet type reference electrode capable of a small size in construction can be easily manufactured and mass-produced, thereby reducing the cost of production and improving its operation and maintenance. Reference mark A designates a substrate formed of materials (in the present preferred embodiment a polyethylene plate) having a sufficiently high electrical insulating property even when immersed in a solution including electrolytes, such as organic high molecular materials, for example, polyethylene, polypropylene, polyethylene terephthalate, acryl, polyfluouroethylene and the like, and inorganic materials, for example, silica glass, Pyrex glass and the like. Electrode D is provided on substrate a by adhering a metal selected from a group comprising electrically conductive Ag, Cu, Au, Pt and the like, alloys thereof and the like, or a paste including these metals, or a semiconductor, such as $IrO_2$ and $SnO_2$, to an upper surface of the substrate A by a physical plating method, such as vacuum deposition method, CVD method, or a chemical plating method, such as an electrolytic method and a non-electrolytic method, or a printing method, such as silk screen method, anastatic printing and flat plate printing (in the present preferred embodiment, the upper surface of the substrate A is subjected to a graft processing and an anchoring process by a silane coupling agent and the like and then, an Ag paste is printed on the upper surface of said substrate A by the silk screen printing method). In addition, a base end portion positioned at one end edge portion of the substrate A as electrode D is formed as the lead portion C as it is. The other nearly circular pointed end portion of the electrode material is positioned at a nearly central portion of the substrate A in the electrode D and is formed as the internal electrode portions B coated with an electrode material, such as AgCl (by physical plating methods of chemical plating methods or printing methods in the same manner as described above).

The substrate A is provided with a support layer F, formed of a material having a sufficiently high electrical insulating property, in the same manner as the substrate A and is also provided with the hole E at a place corresponding to the internal electrode portion B. In the present preferred embodiment, a polyethylene terephthalate layer F can be formed on the upper surface thereof under a condition wherein a lead portion C and its circumference is exposed by, for example, a screen printing method or a hot melting method using adhesives (for example, polyolefine series adhesives, silicon resin series adhesives and the like) capable of securing a sufficiently high electrical insulating property (for example, 10 M or more) or the like. Also the upper surface of this support layer F is subjected to the grafting process and the anchoring process by means of a silane coupling agent and the like.

Hole E in the support layer F is filled with the disc-like gelatinized internal solution formed by adding a gelatinizer (for example, agar-agar, gelatine, glue, alginic acid, various kinds of acrylic water-absorbing polymer and the like) and a gel-evaporation inhibitor (for example, glycerine, ethylene glycol, and the like) to a basic internal solution (for example, obtained by adding a phosphoric acid buffer solution to a 3.3M-aqueous solution of KCl supersaturated with AgCl) by, for example, heating to turn it into a paste and then printing by a screen printing method and the like so that the upper surface of the disc-like gelatinized internal solution G may be slightly projected over the upper surface of said support layer F, and the disc-like gelatinized internal solution G is overlapped on the internal electrode portion B.

In addition, the liquid junction portion above the gelatinized internal solution G in the hole E is covered by a thin film member J formed of $MgF_2$ (or $CaF_2$ as disclosed in Table 1 and Table 2), which is a substance having the fundamental properties of the internal solution G, in short, both a limiting equivalent ionic conductivity of a cation and that of an anion, which are comparatively large, a transport coefficient of the cation and that of the anion nearly equal to each other and a remarkably reduced solubility in water and an aqueous solution (about 1/1000 times that of KCl constructing the internal solution G). Film member J is joined to an upper surface of the support layer F along a circumference thereof so that a lower surface thereof may be contacted to the upper surface of the gelatinized internal solution G.

However, the $MgF_2$ (or $CaF_2$), which forms the thin film member J under a condition infinitely near to a solid condition, becomes a high insulator (dielectric) in the form of a solid (both show an insulating property of about $10^{14} \Omega cm$ under a dried condition) so that the insulating property is adjusted so as to show a moderate value ($10^6$ to $10^8 \Omega cm$).

It is possible to form a crystal of $MgF_2$ (or $CaF_2$) in the form of a remarkably thin film. In this case, since it is necessary to select a thickness of the crystalline thin film itself at about 1,000 A (0.1 microns), an appointed insulating property is given at a thickness of, for example, about 0.1 mm by, for example, vapor coating on one surface side of an ion-response glass thin film or doping Eu and the like.

It is possible to promote the adsorption of moisture in air by increasing a surface area due to the use of crystalline fine powders of $MgF_2$ (or $CaF_2$). In this case, the appointed insulating property is given to the crystalline fine powders having a particle diameter of about 1 to 20 microns at a thickness of, for example, about 0.1 mm by using a biner (such as a silicone resin binder) in such a quantity that the gaps among them are filled under their nearly most closely packed condition.

Figure 10:
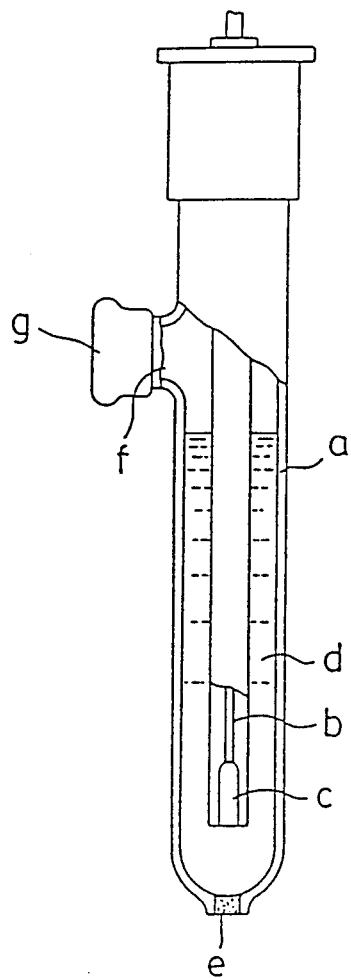
FIG. 10 is a partially sectioned side view showing a reference electrode having a conventional construction for describing the technical background of the present invention and the problems of the prior art.

In addition, the above-described thin film member J formed of $MgF_2$ can be applied in place of the liquid junction member e also in the conventional type reference electrode as shown in said FIG. 10.

Figure 2:
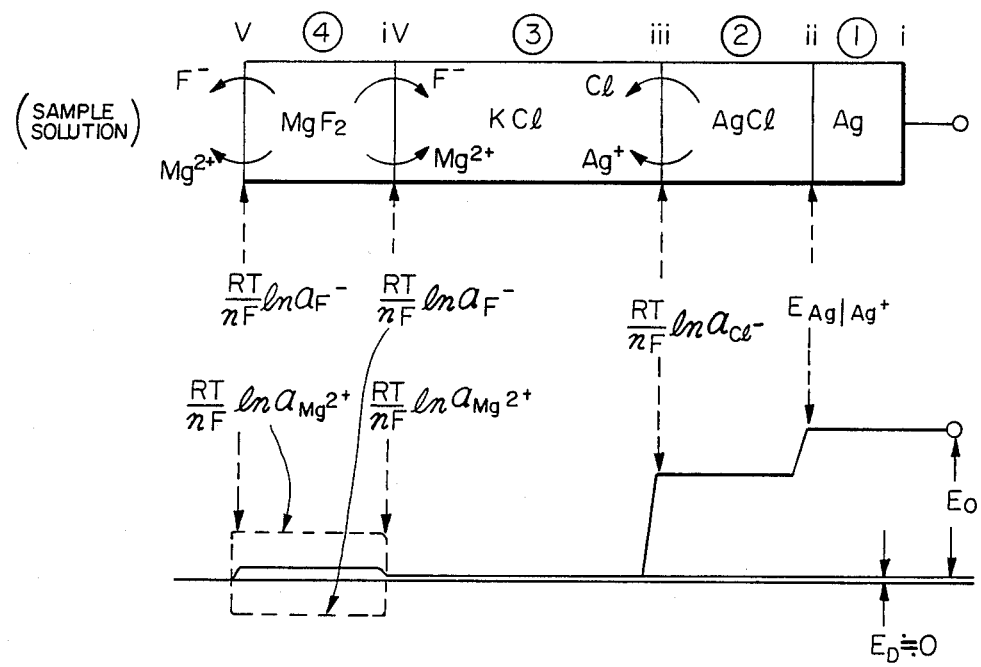
FIG. 2 is a schematic block diagram of FIG. 1.

Now, the reference electrode R constructed in the above-described manner comprises a single pole cell expressed by Ag/AgCl/KCl/$MgF_2$ film/(Sample solution), as shown in a schematic block diagram of FIG. 2. In this schematic block diagram, $E_o$ is a potential generated in an Ag/AgCl/3.3 M-aqueous solution of KCl cell itself (corresponding to a potential difference between iii and i in FIG. 2) and amounts to 204.4 mV relatively to a standard hydrogen electrode at 25° C., and a temperature coefficient is −0.00075 mV/°C. In addition, a potential difference between ④ and ③, in short a potential difference generated on a boundary surface iv, is expressed by the above-described equation of an interliquid potential difference $E_D$, that is to say, $$E_D = (T^+ - T^-) \frac{R \cdot T}{F} \cdot \ln \frac{a_D}{a_{kc}}$$

But, since the transport coefficient $T^+$ of a cation of KCl is substantially equal to the transport coefficient $T^-$ of an anion of KCl, ED amounts nearly to zero. In a range ④, since $MgF_2$ is a dielectric, if a potential difference exists between v and vi, a potential gradient is produced. Also, a potential difference generated on a boundary surface v is expressed by the above-described equation. A potential difference having the same polarity is given as the potential difference between iv and v in respect of $MgF_2$. If $MgF_2$ is a complete dielectric, a potential gradient is produced in the area ④ so that, if ions are transported, a potential gradient is not produced in the same manner as in area ③. That is to say, the potential gradient cannot be sufficiently produced by constructing the thin film member J ($MgF_2$ film) in the above-described manner.

Figure 3:
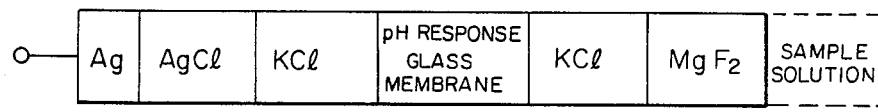
FIG. 3 is a schematic block diagram showing a modified preferred embodiment.

In addition, a modified preferred embodiment of the reference electrode R may be constructed in the form of Ag/AgCl/KCl/pH-response glass film/KCl/$MgF_2$ film/(Sample solution), as shown in FIG. 3. In this case, since the pH-response glass film can be deemed as a $H^+$ ionic electrically conductive film, a potential difference between both sides of the pH-response glass film can be made zero by arranging KCl having the same pH on both sides of the pH-response glass film, thereby obtaining the same result as in the above-described case.

Figure 4:
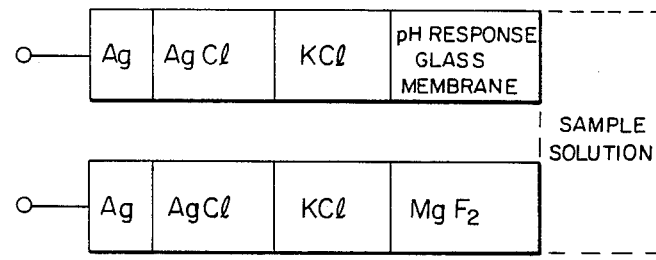
FIG. 4 is a schematic block diagram showing an applied preferred embodiment.

Additionally, in an applied preferred embodiment, an ion concentration-measuring composite electrode can be constructed by combining the reference electrode R having the above-described construction and an ion concentration-measuring electrode, such as a pH-measuring electrode, as shown in FIG. 4.

Figure 5:
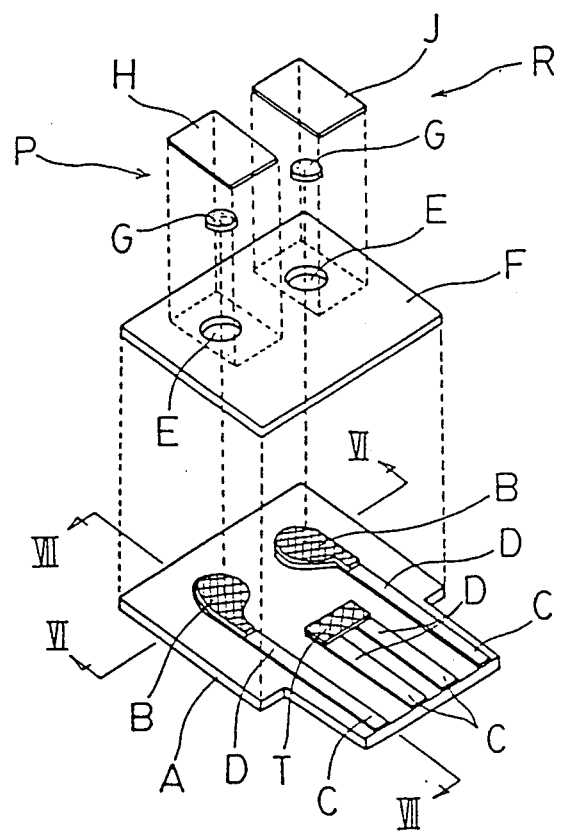
FIG. 5 is an exploded perspective view showing a sheet type pH-measuring composite electrode.
Figure 6:
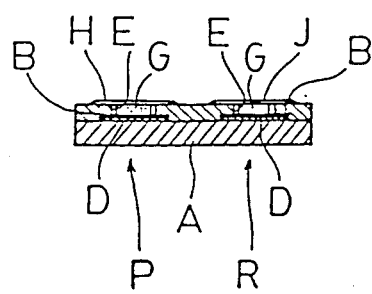
FIG. 6 is a sectional view of FIG. 5 taken along the line VI—VI thereof.
Figure 7:
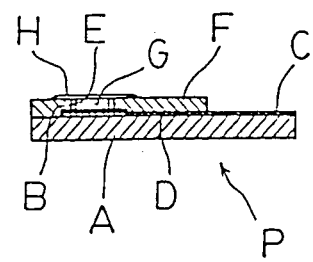
FIG. 7 is a sectional view of FIG. 5 taken along the line VII—VII thereof.
Figure 8:
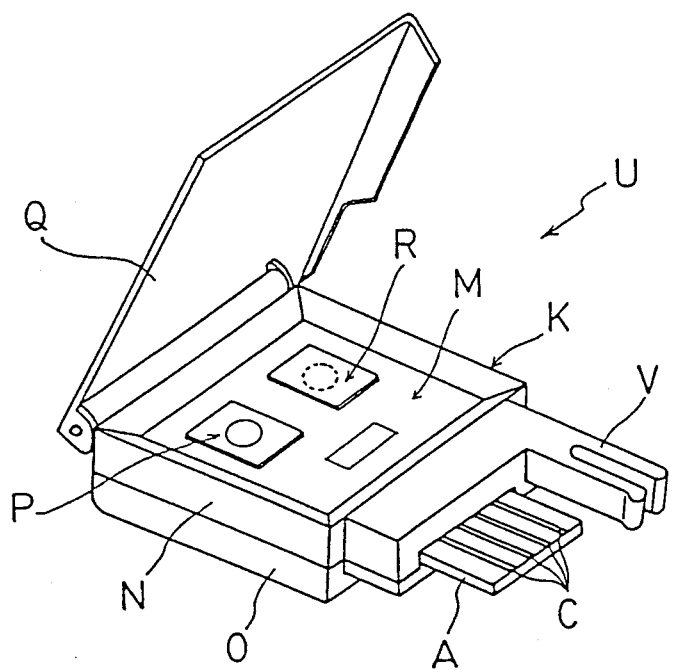
FIG. 8 is a perspective view showing an external appearance of a unit comprising a casing for housing the sheet type pH-measuring composite electrode therein.
Figure 9:
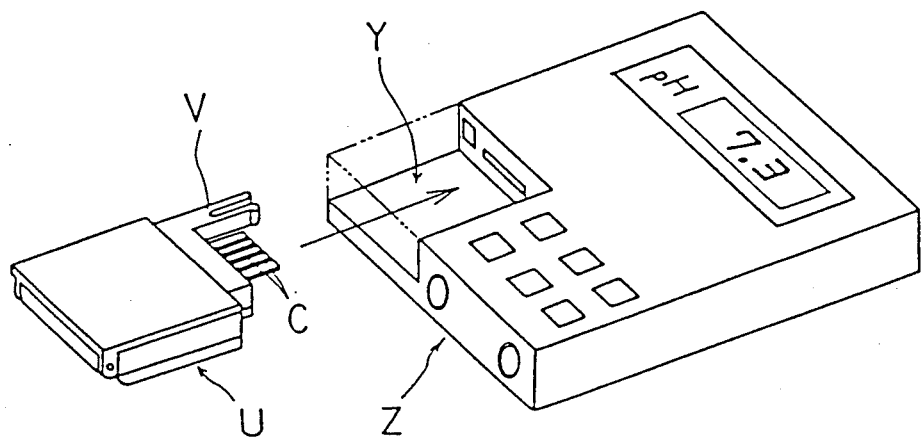
FIG. 9 is a perspective view showing an external appearance of a condition under which the unit is connected to a body of a measuring apparatus.

That is to say, FIGS. 5 to 7 show a sheet type pH-measuring composite electrode according to the applied preferred embodiment. Referring to the exploded perspective view of FIG. 5 as well as FIGS. 6, 7, showing a sectional view of FIG. 5 taken along the line VI—VI and the line VII—VII thereof, reference mark A designates a substrate formed of materials (in the present preferred embodiment a polyethylene plate) having a sufficiently high electrical insulating property even when immersed in a solution including electrolytes, such as organic high molecular materials, for example, polyethylene, polypropylene, polyethylene terephthalate, acryl, polyfluoroethylene and the like, and inorganic materials, for example, silica glass, pyrex glass, and the like, and provided with two pairs of electrode D (inside pair of electrodes and outside pair of electrodes) formed by adhering a metal selected from a group comprising electrically conductive Ag, Cu, Au, Pt and the like, alloys thereof and the like, or a paste including these metals, or a semiconductor, such as $IrO_2$ and $SnO_2$, to an upper surface o the substrate A by a physical plating method, such as a vacuum deposition method and a CVD method, or a chemical plating method, such as an electrolytic method and a non-electrolytic method, or a printing method, such as a silk screen method, anastatic printing and flat plate printing (in the present preferred embodiment the upper surface of the substrate A is subjected to the graft processing and the anchoring process by a silane coupling agent and the like and then, an Ag past is printed on the upper surface of said substrate A by the silk screen printing method). In addition, a base end portion positioned at one end edge portion of the substrate A in every electrode D, is formed as the lead portion C as it is. Besides, the other nearly circular pointed end portion is positioned at a nearly central portion of the substrate A in the outside pair of electrodes D, D to act as internal electrode portions B, B coated with an electrode material, such as AgCl (by physical plating methods or chemical plating methods or printing methods in the same manner as above described), and a temperature-compensating electrode portion T is provided extending between the other pointed end portions positioned at a nearly central portion of the substrate A in the inside pair of electrodes D, D. For example, a thermistor and the like are used as the temperature-compensating electrode portion T.

The substrate A is provided with a support layer F, formed of a material having a sufficiently high electrical insulating property, in the same manner as the substrate A and is also provided with the holes E, E at places corresponding to the internal electrode portions B, B. In the present preferred embodiment, a polyethylene terephthalate layer F can be formed on the upper surface of the substrate thereof under a condition that all of the lead portions C and their circumferences are exposed by, for example, a screen printing method or a hot melting procedure using adhesives (for example, polyolefine series adhesives, silicone resin series adhesives, and the like) capable of securing a sufficiently high electrical insulating property (for example, 10 MΩ or more) or the like. Also, the upper surface of this support layer F is subjected to the grafting process and the anchoring process by means of a silane coupling agent and the like.

Holes E, E of the support layer F are filled with a disc-like gelatinized internal solution G, G formed by adding a gelatinizer (for example, agar-agar, gelatine, glue, alginic acid, various kinds of acrylic water-absorbing polymer and the like) and a gel-evaporation inhibitor (for example, glycerine, ethylene glycol and the like) to a basic internal solution (for example, obtained by adding a phosphoric acid buffer solution to a 3.3M-aqueous solution of KCl supersaturated with AgCl) by, for example, heating to turn it into a paste and then printing by a screen printing method and the like so that the upper surface of the disc-like gelatinized internal solution G, G may be slightly projected over the upper surface of said support layer F, and the disc-like gelatinized internal solution G, G is overlapped on the internal electrode portions B, B.

In addition, above the gelatinized internal solution G is a flat plate-like pH-response glass membrane H, produced by subjecting the flat plate-like super-thin glass previously formed to a predetermined size to the high-speed surface heating treatment, which is also fixedly mounted on the upper surface of the support layer F along the circumference thereof by the use of adhesives I having a sufficiently high electrical insulating property (for example, organic high molecular adhesives, such as silicon series adhesives, epoxy series adhesives, urethane series adhesives and the like, containing a silane coupling agent and the like) so that the lower surface of the flat plate-like pH-response glass membrane H may be contacted to the upper surface of the gelatinized internal solution G and the gelatinized internal solution G may be sealed up tightly in the hole E, to form a pH-measuring glass electrode P.

Besides, in the liquid junction portion above the gelatinized internal solution G in the other hole E, a thin film member J formed of $MgF_2$ (or $CaF_2$), constructed the same as the aforesaid embodiment, is fixedly mounted on the upper surface of the support layer F along the circumference thereof so that the lower surface of the liquid junction membrane J may be contacted to the upper surface of the gelatinized internal solution G to form a reference electrode R.

A pH-measuring sheet type composite electrode constructed in the above-described manner has a thickness of about 0.5 mm in the present preferred embodiment and is housed in a casing K made of synthetic resins so that the pH-measuring glass electrode P and the reference electrode R may be opened toward the upper surface side. One end edge portion of the lead portions C of the substrate A may be protruded toward the outside to form a connection for a modular measuring electrode unit U. The casing K composing the tip-like measuring electrode unit U comprises an upper frame member N forming an indented portion M, into which the sample solution is poured, a bottom cover O of the upper frame member N, and an upper cover Q, which is swingably and closably mounted on one end edge portion of the upper frame member N, of the indented portion M into which the sample solution is poured. In addition, the casing K (in the present preferred embodiment, a portion of the upper frame member) is provided with an engaging projection V, for insertion into an opening in device body Z, which will be mentioned later.

With the tip-like measuring electrode unit U including the pH-measuring sheet type composite electrode having the above-described construction, a sample solution of one drop to several drops is poured into the indented or recessed portion M after opening the upper cover Q to expose the pH-measuring glass electrode P and the reference electrode R positioned on a bottom portion of the indented portion M into sufficient contact with the sample solution and then, the upper cover Q is closed. Subsequently, the tip-like measuring electrode unit U is inserted into a complementarily fitting portion Y of the measuring device body Z for electrical connection of the lead portions C and for engaging projection V to measure the pH of the sample solution.

In accordance with the present invention, a reference electrode having a liquid junction portion is provided with a this film member formed of $MgF_2$ or $CaF_2$ which are substances having both a transport coefficient of a cation and a transport coefficient of an anion nearly equal to each other and a remarkably reduced solubility in water and an aqueous solution, so that superior effects can be exhibited. The prior art problem of leakage of an internal solution is almost completely prevented and the inter-liquid differential potential problem can be remarkably reduced and stabilized, thereby securing a remarkably high accuracy of measurement and reliability. In addition, the internal solution and the liquid junction portion can be easily maintained under an excellent condition for a long period of time without carrying out the previous troublesome operations that have been conventionally required, that is to say, it is remarkably advantageous also in maintenance, operation and the like.

What is claimed is:

1. A reference electrode comprising a liquid junction portion having a film member in a plate-like configuration to act as a liquid junction member for a sheet-type electrode and formed of $MgF_2$ or CaF2, which are substances having both a transport coefficient of a cation and a transport coefficient of an anion substantially equal to each other with a low solubility in water and an aqueous solution, said film member being formed from crystalline powder having a particle diameter of about 1 to 20 microns.

2. The invention of claim 1 wherein the liquid junction member is a film crystal of approximately 0.1 microns in thickness.

3. The invention of claim 1 wherein the liquid junction member is a crystalline powder of about 1 to 20 microns in diameter supported in an inert binder having a thickness of about 0.1 mm.

4. A sheet-type electrode assembly for measuring a property of a test specimen, comprising:
a support layer;
means for providing a pair of electrical contacts on the support layer;
means for supporting internal solutions in contact with the electrical contacts, and
means for providing a reference electrode interface including a plate-like contact member constructed of one of $CaF_2$ and $MgF_2$ having a transfer coefficient of a cation and a transfer coefficient of an anion substantially equal to each other, said contact member having particles whose diameters are about 20 microns or less and an overall thickness of about 0.1 mm, said interface being sufficient to stabilize an inter-liquid differential potential.

5. The invention of claim 4 wherein the contact member is selected from the family of $MgF_2$ and $CaF_2$.

6. The invention of claim 5 wherein the contact member is a plate member.

7. The invention of claim 5 wherein the contact member is a film crystal of approximately 0.1 microns in thickness.

8. The invention of claim 5 wherein the contact member is a crystalline powder of about 1 to 20 microns in diameter supported in an inert binder having a thickness of about 0.1 mm.

9. In a sheet-type reference electrode having an electrode layered between an insulating substrate and an insulating support layer, said support later defining a hole therethrough, a gelatinized internal solution in said hole, and an improved liquid junction, wherein the improvement comprises:
a planar film member for contacting said gelatinized internal solution and a sample solution, said film member being adherable to a top side of said support layer and constructed of crystalline powder of one of $CaF_2$ and $MgF_2$ said powder having a particle diameter of about 1 to 20 microns, said film member having a solubility of about 1/1,000 times that of KCL in water and aqueous solutions, and providing a stabilized inter-liquid differential potential.

10. The improvement according to claim 9 wherein said film member has a transfer coefficient of a cation and a transfer coefficient of an anion within about ±0.1 of each other.

11. The improvement according to claim 9 wherein said film member has a thickness of about 0.1 microns.

12. The improvement according to claim 9 wherein said film member prevents substantially any leakage of said internal solution into said sample solution.

* * * * *